United States Patent [19]

Kolassa et al.

[11] Patent Number: 4,880,456
[45] Date of Patent: Nov. 14, 1989

[54] CYCLOHEXENONE DERIVATIVES, THEIR PREPARATION AND THEIR USE FOR CONTROLLING UNDESIRABLE PLANT GROWTH

[75] Inventors: Dieter Kolassa, Ludwigshafen; Michael Keil, Freinsheim; Ulrich Schirmer, Heidelberg; Hans Theobald, Limburgerhof; Rainer Becker, Bad Duerkheim; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 26,378

[22] Filed: Mar. 16, 1987

[30] Foreign Application Priority Data

Mar. 19, 1986 [DE] Fed. Rep. of Germany ....... 3609181

[51] Int. Cl.$^4$ .................... C07D 261/08; A01N 43/80
[52] U.S. Cl. ......................................... 71/88; 548/247
[58] Field of Search ...................... 71/88, 90; 548/247

[56] References Cited

U.S. PATENT DOCUMENTS

| 4,624,696 | 11/1986 | Keil et al. | 71/88 |
| 4,704,157 | 11/1987 | Conway et al. | 71/90 |
| 4,761,486 | 8/1988 | Zeeh et al. | 71/88 |

FOREIGN PATENT DOCUMENTS

| 123001 | 10/1984 | European Pat. Off. |
| 162224 | 11/1985 | European Pat. Off. |
| 2822304 | 11/1978 | Fed. Rep. of Germany. |
| 3121355 | 12/1982 | Fed. Rep. of Germany. |

*Primary Examiner*—Mukund J. Shah
*Assistant Examiner*—E. Bernhardt
*Attorney, Agent, or Firm*—Oblon, Spivak, McClelland, Maier & Neustadt

[57] ABSTRACT

Cyclohexenone derivatives of the formula

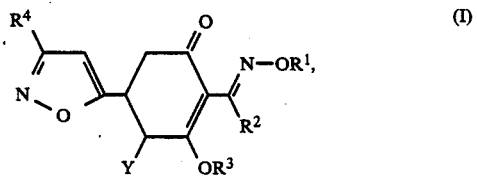

where
$R^1$ is alkyl, alkenyl, alkynyl, haloalkyl or haloalkenyl, alkoxyalkyl, unsubstituted or substituted cycloalkylmethyl, unsubstituted or substituted benzyl, or is a 5-membered heterocyclic ring which is bonded to the oxygen via a methylene unit,
$R^2$ is alkyl, $R^3$ is hydrogen, alkylcarbonyl, alkenylcarbonyl, unsubstituted or substituted benzoyl, trialkylsilyl, alkyl- or arylsulfonyl, dialkylphosphono or -thiophosphono, or an organic or inorganic cation,
$R^4$ is unsubstituted or substituted alkyl, alkenyl or alkynyl, or unsubstituted or substituted cycloalkyl, and
Y is hydrogen, methoxycarbonyl, cyano, alkyl or halogen, and herbicides containing these compounds.

7 Claims, No Drawings

CYCLOHEXENONE DERIVATIVES, THEIR PREPARATION AND THEIR USE FOR CONTROLLING UNDESIRABLE PLANT GROWTH

The present invention relates to cyclohexenone derivatives, their preparation, and herbicides which contain these compounds as active ingredients.

The herbicidal action of 3-hydroxy-2-cyclohexen-1-one oxime ether derivatives which carry a five-membered heterocyclic radical in the 5-position is disclosed in European Pat. Nos. 162,224 and 125,094.

We have found that cyclohexenone derivatives of the formula

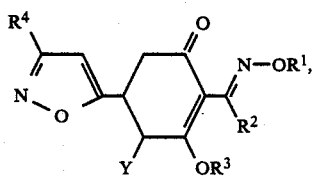

where $R^1$ is alkyl of 1 to 4 carbon atoms, alkenyl of 3 or 4 carbon atoms, alkynyl of 3 or 4 carbon atoms, haloalkyl or haloalkenyl of 2 to 4 carbon atoms and 1 to 3 halogen atoms, alkoxyalkyl of 2 to 4 carbon atoms, cycloalkylmethyl of 4 to 7 carbon atoms, unsubstituted or substituted by $C_1$-$C_4$-alkyl or halogen, or is benzyl which is unsubstituted or substituted by $C_1$-$C_4$-alkyl, $C_1$-$C_4$-alkoxy, $C_1$-$C_4$-alkylthio, halogen, cyano, trifluoromethyl or nitro, or is a 5-membered heterocyclic ring which is bonded to the oxygen via a methylene unit and may contain 1 or 2 hetero atoms from the group consisting of N, O and S and up to 2 double bonds and up to 2 substituents from the group consisting of $C_1$-$C_4$-alkyl, $C_1$-$C_4$-alkoxy or halogen, $R^2$ is alkyl of 1 to 4 carbon atoms, $R^3$ is hydrogen, alkylcarbonyl of 1 to 20 carbon atoms, alkenylcarbonyl of 1 to 20 carbon atoms which contains a double bond, or benzoyl which is unsubstituted or substituted by $C_1$-$C_8$-alkyl, or is trialkylsilyl where alkyl is of 1 to 4 carbon atoms, alkyl- or arylsulfonyl of 1 to 7 carbon atoms, dialkylphosphono or -thiophosphono where each alkyl radical is of 1 to 4 carbon atoms, or an organic or inorganic cation, $R^4$ is the $C_2$-$C_{20}$-alkyl, alkenyl or alkynyl, where the carbon chain may contain up to two double bonds or triple bonds and may be substituted by $C_1$-$C_4$-alkyl, $C_1$-$C_4$-alkoxy or $C_1$-$C_4$-alkylthio, or is $C_3$-$C_6$-cycloalkyl, unsubstituted or substituted by $C_1$-$C_4$-alkyl, $C_1$-$C_4$-alkoxy or $C_1$-$C_4$-alkylthio, or is $C_3$-$C_8$-alkyl having 2 O or S atoms on the alkyl chain, or methyl which is substituted by $C_1$-$C_4$-alkoxy or $C_1$-$C_4$-alkylthio, and Y is hydrogen, methoxycarbonyl, cyano, alkyl or halogen, have a good herbicidal action, preferably against species from the family consisting of the grasses (Gramineae). They are tolerated and therefore selective in broad-leaved crops and in monocotyledon plants not belonging to the Gramineae. Some compounds also have a selective action in gramineous crops, e.g. wheat, and also control undesirable grasses.

Examples of radicals $R^1$ in formula I are methyl, ethyl, n-propyl, allyl, (E)-2-butenyl, 2-fluoroethyl, 2-chloroethyl, (E)-3-chloro-2-propenyl, 2,3,3-trichloro-2-propenyl, propargyl, methoxymethyl, methoxyethyl, 3,3-dichlorocyclopropylmethyl, 3-chlorobenzyl, 4-cyanobenzyl, 3-methyl-5-isoxazolylmethyl, 5-chloro-2-thenyl and 5-bromo-2-thenyl. Thenyl=methylenethienyl.

In formula I, $R^2$ is straight-chain or branched alkyl of 1 to 4 carbon atoms, i.e. methyl, ethyl, n-propyl, isopropyl, n-butyl, sec-butyl, isobutyl or tert-butyl.

Examples of $R^3$ are hydrogen, acetyl, propionyl, butyryl, isobutyryl, pivaloyl, valeroyl, caproyl, caprinoyl, lauroyl, palmitoyl, stearoyl, oleoyl, benzoyl, 4-hexylbenzoyl, methylsulfonyl, p-tolylsulfonyl, trimethylsilyl, diethylphosphono and diethylthiophosphono, as well as alkali metal cations, in particular sodium and potassium, alkaline earth metal cations, in particular calcium, magnesium and barium, and manganese, copper, zinc and iron cations as well as ammonium, phosphonium, sulfonium and sulfoxonium cations, such as ammonium, tetraalkylammonium, benzyltrialkylammonium, trialkylsulfonium or trialkylsulfoxonium.

Examples of $R^4$ are $C_2$-$C_{10}$-alkyl, ethyl, n-propyl, isopropyl, n-butyl, sec-butyl, tert-butyl, iso-butyl, 2,4,4-trimethylpentyl, 1-ethylpentyl, 2,6-dimethylheptyl, cyclopropyl, cyclohexyl, methoxymethyl, ethoxymethyl, methylthiomethyl, ethylthiomethyl, 1-methoxyethyl, 2-methylthioethyl, 1,3-dimethoxypropyl, 2-ethoxyethyl, 1-methyl-2-methylthioethyl, 2-methyl-1-methylthiomethylpropyl, 1-methylthiomethylbutyl and 2-methyl-1-propenyl.

Examples of Y are hydrogen, methoxycarbonyl, cyano, methyl and chlorine.

The cyclohexenone derivatives of the formula I can be obtained by reacting a compound of the formula II

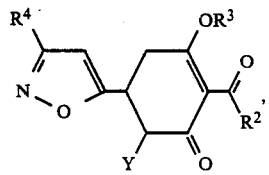

where $R^2$, $R^3$, $R^4$ and Y have the above meanings, with alkoxyammonium compounds of the formula $R^1ONH_2 \cdot HX$, where X is an anion. To do this, the two reactants are reacted in a solvent in the presence of a base at an adequate temperature, which may be from 0° C. to the boiling point of the solvent. Examples of suitable bases are carbonates, bicarbonates, acetates, alcoholates, oxides and hydroxides of alkali metals or alkaline earth metals, in particular of sodium, potassium, magnesium or calcium, and organic bases, such as pyridine or tertiary amines.

Examples of suitable solvents are dimethyl sulfoxide, alcohols, such as methanol, ethanol or isopropanol, aromatic hydrocarbons, such as benzene or toluene, chlorohydrocarbons, such as chloroform or dichloroethane, aliphatic hydrocarbons, such as hexane or cyclohexane, esters, such as ethyl acetate, and ethers, such as dioxane or tetrahydrofuran.

The reaction is complete after a few hours, and the reaction product can be isolated by evaporating down the mixture, partitioning the residue in methylene chloride/water and distilling off the solvent under reduced pressure.

The compounds of the formula I can also be obtained by reacting a compound II with an appropiate alkoxyamine of the formula $R^1ONH_2$ in a suitable diluent, a suitable reaction temperature being, for example, from 15° to 70° C. The alkoxyamine can be used in the form of an aqueous solution; depending on the solvent used for the other reactant, a single-phase or two-phase reaction mixture is obtained.

Examples of suitable solvents for this reaction are alcohols, such as methanol, ethanol, isopropanol or cyclohexanol, aliphatic and aromatic hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

Alkali metal salts of the compounds I can be obtained by treating a 3-hydroxy compound with sodium or potassium hydroxide or alcoholate in aqueous solution or in an organic solvent, such as methanol, ethanol, acetone or toluene.

Other metal salts, for example the manganese, copper, zinc, iron, calcium, magnesium and barium salts, can be prepared from the sodium salts in a conventional manner, and ammonium and phosphonium salts can be obtained in a similar manner using ammonia or phosphonium, sulfonium or sulfoxonium hydroxides.

The compounds I can be prepared, for example, from the corresponding cyclohexane-1,3-diones of the formula II

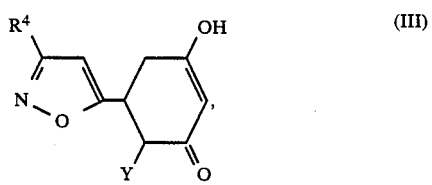

by a conventional method [Tetrahedron Lett. (1975), 2491].

It is also possible to prepare compounds of the formula I via the enol ester intermediates, which are obtained in the reaction of compounds of the formula III with acyl chlorides in the presence of bases and are subsequently subjected to a rearrangement reaction with certain imidazole or pyridine derivatives (Japanese Preliminary Published Application 79/063052).

The compounds of the formula I are obtained by a conventional process, as is evident from the scheme below. Z is a 5-isoazolyl radical which is substituted in the 3-position by $R^4$.

Suitable starting materials are the 5-chloromethylisoxazoles $Z$-$CH_2$-Cl, which are obtainable by subjecting propargyl chloride to a 1,3-dipolar cycloaddition reaction with hydroxamoyl chlorides or nitrile oxides. The methods usually employed for this purpose are known.

The compounds which contain another halogen atom in place of the chlorine are also suitable.

The chloromethylisoxazole $Z$-$CH_2$-Cl is converted to the 5-formylisoxazoles $Z$-CHO by a conventional method, via the 5-hydroxymethyl intermediate or by a direct route, the said formylisoxazoles also being possible starting materials.

The Example which follows illustrates the preparation of the novel compounds. Parts by weight bear the same relation to parts by volume as that of the kilogram to the liter.

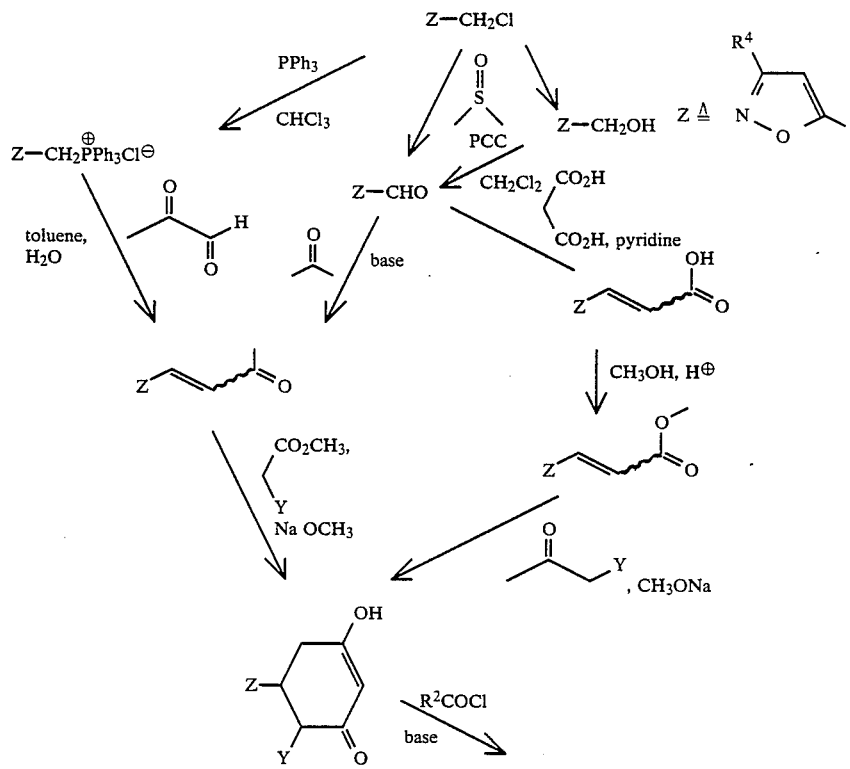

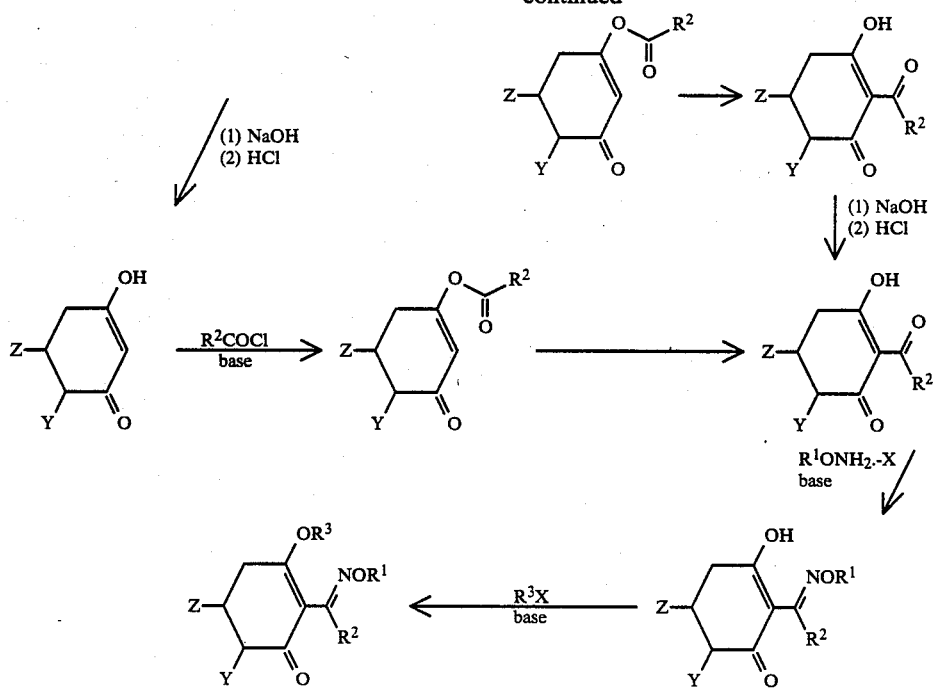

EXAMPLE

A mixture of 30.0 g (0.11 mole) of 3-hydroxy-5-(3-isopropylisoxazolyl)-2-propionyl-2-cyclohexen-1-one, 10.1 g (0.12 mole) of sodium bicarbonate and 11.7 g (0.12 mole) of ethoxyamine hydrochloride in 350 ml of ethanol is stirred for 1 h at room temperature. Thereafter, the solvent is separated off, the residue is stirred in 300 ml of ice water, and the product is filtered off under suction, washed with water and dried under reduced pressure. 29 g (82% of theory) of a beige solid of melting point 84°–85° C. are obtained (active ingredient 29).

The compounds of the formula I which are listed in the table and characterized by their melting point (mp.) can be prepared in a similar manner. Their $^1$H NMR data and elemental analyses are reproduced in Table 2. Compounds for which no physical data are given can be obtained by similar methods.

The $^1$H NMR spectra were recorded in deuteriochloroform or hexadeuteriosulfoxide as the solvent, using tetramethylsilane as the internal standard. The chemical shifts are recorded in ppm. The multiplicities are stated as follows: s=singlet, d=doublet, t=triplet, q=quartet and m=multiplet.

TABLE 1

| | | List of active ingredients | | | |
|---|---|---|---|---|---|
| | $R^4$ | $R^3$ | $R^2$ | $R^1$ | Mp/°C. |
| 1 | ethyl | H | methyl | ethyl | |
| 2 | ethyl | H | methyl | allyl | |
| 3 | ethyl | H | methyl | (E)—3-chloro-2-propenyl | |
| 4 | ethyl | H | methyl | (E)—2-butenyl | |
| 5 | ethyl | H | ethyl | ethyl | 79–81 |
| 6 | ethyl | H | ethyl | allyl | 61–63 |
| 7 | ethyl | H | ethyl | (E)—3-chloro-2-propenyl | 86–88 |
| 8 | ethyl | H | ethyl | (E)—2-butenyl | 80–82 |
| 9 | ethyl | H | n-propyl | ethyl | |
| 10 | ethyl | H | n-propyl | allyl | |
| 11 | ethyl | H | n-propyl | (E)—3-chloro-2-propenyl | |
| 12 | ethyl | H | n-propyl | (E)—2-butenyl | |
| 13 | n-propyl | H | methyl | ethyl | |
| 14 | n-propyl | H | methyl | allyl | |
| 15 | n-propyl | H | methyl | (E)—3-chloro-2-propenyl | |
| 16 | n-propyl | H | methyl | (E)—2-butenyl | |
| 17 | n-propyl | H | ethyl | ethyl | |
| 18 | n-propyl | H | ethyl | allyl | |
| 19 | n-propyl | H | ethyl | (E)—3-chloro-2-propenyl | |
| 20 | n-propyl | H | ethyl | (E)—2-butenyl | |
| 21 | n-propyl | H | n-propyl | ethyl | |
| 22 | n-propyl | H | n-propyl | allyl | |
| 23 | n-propyl | H | n-propyl | (E)—3-chloro-2-propenyl | |
| 24 | n-propyl | H | n-propyl | (E)—2-butenyl | |
| 25 | i-propyl | H | methyl | ethyl | |
| 26 | i-propyl | H | methyl | allyl | 78–80 |
| 27 | i-propyl | H | methyl | (E)—3-chloro-2-propenyl | |
| 28 | i-propyl | H | methyl | (E)—2-butenyl | |
| 29 | i-propyl | H | ethyl | ethyl | 84–85 |

TABLE 1-continued

List of active ingredients

| | R⁴ | R³ | R² | R¹ | Mp/°C. |
|---|---|---|---|---|---|
| 30 | i-propyl | H | ethyl | allyl | 71–74 |
| 31 | i-propyl | H | ethyl | (E)—3-chloro-2-propenyl | 103–106 |
| 32 | i-propyl | H | ethyl | (E)—2-butenyl | 107–110 |
| 33 | i-propyl | H | n-propyl | ethyl | 60–61 |
| 34 | i-propyl | H | n-propyl | allyl | |
| 35 | i-propyl | H | n-propyl | (E)—3-chloro-2-propenyl | |
| 36 | i-propyl | H | n-propyl | (E)—2-butenyl | 80–84 |
| 37 | n-butyl | H | methyl | ethyl | |
| 38 | n-butyl | H | methyl | allyl | |
| 39 | n-butyl | H | methyl | (E)—3-chloro-2-propenyl | |
| 40 | n-butyl | H | methyl | (E)—2-butenyl | |
| 41 | n-butyl | H | ethyl | ethyl | |
| 42 | n-butyl | H | ethyl | allyl | |
| 43 | n-butyl | H | ethyl | (E)—3-chloro-2-propenyl | |
| 44 | n-butyl | H | ethyl | (E)—2-butenyl | |
| 45 | n-butyl | H | n-propyl | ethyl | |
| 46 | n-butyl | H | n-propyl | allyl | |
| 47 | n-butyl | H | n-propyl | (E)—3-chloro-2-propenyl | |
| 48 | n-butyl | H | n-propyl | (E)—2-butenyl | |
| 49 | s-butyl | H | methyl | ethyl | |
| 50 | s-butyl | H | methyl | allyl | |
| 51 | s-butyl | H | methyl | (E)—3-chloro-2-propenyl | |
| 52 | s-butyl | H | methyl | (E)—2-butenyl | |
| 53 | s-butyl | H | ethyl | ethyl | |
| 54 | s-butyl | H | ethyl | allyl | |
| 55 | s-butyl | H | ethyl | (E)—3-chloro-2-propenyl | |
| 56 | s-butyl | H | ethyl | (E)—2-butenyl | |
| 57 | s-butyl | H | n-propyl | ethyl | |
| 58 | s-butyl | H | n-propyl | allyl | |
| 59 | s-butyl | H | n-propyl | (E)—3-chloro-2-propenyl | |
| 60 | s-butyl | H | n-propyl | (E)—2-butenyl | |
| 61 | t-butyl | H | methyl | ethyl | |
| 62 | t-butyl | H | methyl | allyl | |
| 63 | t-butyl | H | methyl | (E)—3-chloro-2-propenyl | |
| 64 | t-butyl | H | methyl | (E)—2-butenyl | |
| 65 | t-butyl | H | ethyl | ethyl | 94–97 |
| 66 | t-butyl | H | ethyl | allyl | 92–94 |
| 67 | t-butyl | H | ethyl | (E)—3-chloro-2-propenyl | 120–122 |
| 68 | t-butyl | H | ethyl | (E)—2-butenyl | 110–113 |
| 69 | t-butyl | H | n-propyl | ethyl | 75–78 |
| 70 | t-butyl | H | n-propyl | allyl | 83–85 |
| 71 | t-butyl | H | n-propyl | (E)—3-chloro-2-propenyl | 128–131 |
| 72 | t-butyl | H | n-propyl | (E)—2-butenyl | 118–120 |
| 73 | i-butyl | H | methyl | ethyl | |
| 74 | i-butyl | H | methyl | allyl | |
| 75 | i-butyl | H | methyl | (E)—3-chloro-2-propenyl | |
| 76 | i-butyl | H | methyl | (E)—2-butenyl | |
| 77 | i-butyl | H | ethyl | ethyl | |
| 78 | i-butyl | H | ethyl | allyl | |
| 79 | i-butyl | H | ethyl | (E)—3-chloro-2-propenyl | |
| 80 | i-butyl | H | ethyl | (E)—2-butenyl | |
| 81 | i-butyl | H | n-propyl | ethyl | |
| 82 | i-butyl | H | n-propyl | allyl | |
| 83 | i-butyl | H | n-propyl | (E)—3-chloro-2-propenyl | |
| 84 | i-butyl | H | n-propyl | (E)—2-butenyl | |
| 85 | 2,4,4-trimethyl-pentyl | H | methyl | ethyl | |
| 86 | 2,4,4-trimethyl-pentyl | H | methyl | allyl | |
| 87 | 2,4,4-trimethyl-pentyl | H | methyl | (E)—3-chloro-2-propenyl | |
| 88 | 2,4,4-trimethyl-pentyl | H | methyl | (E)—2-butenyl | |
| 89 | 2,4,4-trimethyl-pentyl | H | ethyl | ethyl | |
| 90 | 2,4,4-trimethyl-pentyl | H | ethyl | allyl | |
| 91 | 2,4,4-trimethyl-pentyl | H | ethyl | (E)—3-chloro-2-propenyl | |
| 92 | 2,4,4-trimethyl-pentyl | H | ethyl | (E)—2-butenyl | |
| 93 | 2,4,4-trimethyl-pentyl | H | n-propyl | ethyl | |
| 94 | 2,4,4-trimethyl-pentyl | H | n-propyl | allyl | |
| 95 | 2,4,4-trimethyl-pentyl | H | n-propyl | (E)—3-chloro-2-propenyl | |
| 96 | 2,4,4-trimethyl-pentyl | H | n-propyl | (E)—2-butenyl | |
| 97 | 1-ethylpentyl | H | methyl | ethyl | |

TABLE 1-continued

List of active ingredients

| | R⁴ | R³ | R² | R¹ | Mp/°C. |
|---|---|---|---|---|---|
| 98 | 1-ethylpentyl | H | methyl | allyl | |
| 99 | 1-ethylpentyl | H | methyl | (E)—3-chloro-2-propenyl | |
| 100 | 1-ethylpentyl | H | methyl | (E)—2-butenyl | |
| 101 | 1-ethylpentyl | H | ethyl | ethyl | |
| 102 | 1-ethylpentyl | H | ethyl | allyl | |
| 103 | 1-ethylpentyl | H | ethyl | (E)—3-chloro-2-propenyl | |
| 104 | 1-ethylpentyl | H | ethyl | (E)—2-butenyl | |
| 105 | 1-ethylpentyl | H | n-propyl | ethyl | |
| 106 | 1-ethylpentyl | H | n-propyl | allyl | |
| 107 | 1-ethylpentyl | H | n-propyl | (E)—3-chloro-2-propenyl | |
| 108 | 1-ethylpentyl | H | n-propyl | (E)—2-butenyl | |
| 109 | 2,6-dimethylheptyl | H | methyl | ethyl | |
| 110 | 2,6-dimethylheptyl | H | methyl | allyl | |
| 111 | 2,6-dimethylheptyl | H | methyl | (E)—3-chloro-2-propenyl | |
| 112 | 2,6-dimethylheptyl | H | methyl | (E)—2-butenyl | |
| 113 | 2,6-dimethylheptyl | H | ethyl | ethyl | |
| 114 | 2,6-dimethylheptyl | H | ethyl | allyl | |
| 115 | 2,6-dimethylheptyl | H | ethyl | (E)—3-chloro-2-propenyl | |
| 116 | 2,6-dimethylheptyl | H | ethyl | (E)—2-butenyl | |
| 117 | 2,6-dimethylheptyl | H | n-propyl | ethyl | |
| 118 | 2,6-dimethylheptyl | H | n-propyl | allyl | |
| 119 | 2,6-dimethylheptyl | H | n-propyl | (E)—3-chloro-2-propenyl | |
| 120 | 2,6-dimethylheptyl | H | n-propyl | (E)—2-butenyl | |
| 121 | cyclopropyl | H | methyl | ethyl | |
| 122 | cyclopropyl | H | methyl | allyl | |
| 123 | cyclopropyl | H | methyl | (E)—3-chloro-2-propenyl | |
| 124 | cyclopropyl | H | methyl | (E)—2-butenyl | |
| 125 | cyclopropyl | H | ethyl | ethyl | |
| 126 | cyclopropyl | H | ethyl | allyl | |
| 127 | cyclopropyl | H | ethyl | (E)—3-chloro-2-propenyl | |
| 128 | cyclopropyl | H | ethyl | (E)—2-butenyl | |
| 129 | cyclopropyl | H | n-propyl | ethyl | |
| 130 | cyclopropyl | H | n-propyl | allyl | |
| 131 | cyclopropyl | H | n-propyl | (E)—3-chloro-2-propenyl | |
| 132 | cyclopropyl | H | n-propyl | (E)—2-butenyl | |
| 133 | cyclohexyl | H | methyl | ethyl | |
| 134 | cyclohexyl | H | methyl | allyl | |
| 135 | cyclohexyl | H | methyl | (E)—3-chloro-2-propenyl | |
| 136 | cyclohexyl | H | methyl | (E)—2-butenyl | |
| 137 | cyclohexyl | H | ethyl | ethyl | |
| 138 | cyclohexyl | H | ethyl | allyl | |
| 139 | cyclohexyl | H | ethyl | (E)—3-chloro-2-propenyl | |
| 140 | cyclohexyl | H | ethyl | (E)—2-butenyl | |
| 141 | cyclohexyl | H | n-propyl | ethyl | |
| 142 | cyclohexyl | H | n-propyl | allyl | |
| 143 | cyclohexyl | H | n-propyl | (E)—3-chloro-2-propenyl | |
| 144 | cyclohexyl | H | n-propyl | (E)—2-butenyl | |
| 145 | methoxymethyl | H | methyl | ethyl | |
| 146 | methoxymethyl | H | methyl | allyl | |
| 147 | methoxymethyl | H | methyl | (E)—3-chloro-2-propenyl | |
| 148 | methoxymethyl | H | methyl | (E)—2-butenyl | |
| 149 | methoxymethyl | H | ethyl | ethyl | |
| 150 | methoxymethyl | H | ethyl | allyl | |
| 151 | methoxymethyl | H | ethyl | (E)—3-chloro-2-propenyl | |
| 152 | methoxymethyl | H | ethyl | (E)—2-butenyl | |
| 153 | methoxymethyl | H | n-propyl | ethyl | |
| 154 | methoxymethyl | H | n-propyl | allyl | |
| 155 | methoxymethyl | H | n-propyl | (E)—3-chloro-2-propenyl | |
| 156 | methoxymethyl | H | n-propyl | (E)—2-butenyl | |
| 157 | ethoxymethyl | H | methyl | ethyl | |
| 158 | ethoxymethyl | H | methyl | allyl | |
| 159 | ethoxymethyl | H | methyl | (E)—3-chloro-2-propenyl | |
| 160 | ethoxymethyl | H | methyl | (E)—2-butenyl | |
| 161 | ethoxymethyl | H | ethyl | ethyl | |
| 162 | ethoxymethyl | H | ethyl | allyl | |
| 163 | ethoxymethyl | H | ethyl | (E)—3-chloro-2-propenyl | |
| 164 | ethoxymethyl | H | ethyl | (E)—2-butenyl | |
| 165 | ethoxymethyl | H | n-propyl | ethyl | |
| 166 | ethoxymethyl | H | n-propyl | allyl | |
| 167 | ethoxymethyl | H | n-propyl | (E)—3-chloro-2-propenyl | |
| 168 | ethoxymethyl | H | n-propyl | (E)—2-butenyl | |
| 169 | methylthiomethyl | H | methyl | ethyl | |
| 170 | methylthiomethyl | H | methyl | allyl | |
| 171 | methylthiomethyl | H | methyl | (E)—3-chloro-2-propenyl | |
| 172 | methylthiomethyl | H | methyl | (E)—2-butenyl | |
| 173 | methylthiomethyl | H | ethyl | ethyl | |
| 174 | methylthiomethyl | H | ethyl | allyl | |
| 175 | methylthiomethyl | H | ethyl | (E)—3-chloro-2-propenyl | |
| 176 | methylthiomethyl | H | ethyl | (E)—2-butenyl | |
| 177 | methylthiomethyl | H | n-propyl | ethyl | |

TABLE 1-continued

List of active ingredients

| | R⁴ | R³ | R² | R¹ | Mp/°C. |
|---|---|---|---|---|---|
| 178 | methylthiomethyl | H | n-propyl | allyl | |
| 179 | methylthiomethyl | H | n-propyl | (E)—3-chloro-2-propenyl | |
| 180 | methylthiomethyl | H | n-propyl | (E)—2-butenyl | |
| 181 | ethylthiomethyl | H | methyl | ethyl | |
| 182 | ethylthiomethyl | H | methyl | allyl | |
| 183 | ethylthiomethyl | H | methyl | (E)—3-chloro-2-propenyl | |
| 184 | ethylthiomethyl | H | methyl | (E)—2-butenyl | |
| 185 | ethylthiomethyl | H | ethyl | ethyl | |
| 186 | ethylthiomethyl | H | ethyl | allyl | |
| 187 | ethylthiomethyl | H | ethyl | (E)—3-chloro-2-propenyl | |
| 188 | ethylthiomethyl | H | ethyl | (E)—2-butenyl | |
| 189 | ethylthiomethyl | H | n-propyl | ethyl | |
| 190 | ethylthiomethyl | H | n-propyl | allyl | |
| 191 | ethylthiomethyl | H | n-propyl | (E)—3-chloro-2-propenyl | |
| 192 | ethylthiomethyl | H | n-propyl | (E)—2-butenyl | |
| 193 | 1-methoxyethyl | H | methyl | ethyl | |
| 194 | 1-methoxyethyl | H | methyl | allyl | |
| 195 | 1-methoxyethyl | H | methyl | (E)—3-chloro-2-propenyl | |
| 196 | 1-methoxyethyl | H | methyl | (E)—2-butenyl | |
| 197 | 1-methoxyethyl | H | ethyl | ethyl | |
| 198 | 1-methoxyethyl | H | ethyl | allyl | |
| 199 | 1-methoxyethyl | H | ethyl | (E)—3-chloro-2-propenyl | |
| 200 | 1-methoxyethyl | H | ethyl | (E)—2-butenyl | |
| 201 | 1-methoxyethyl | H | n-propyl | ethyl | |
| 202 | 1-methoxyethyl | H | n-propyl | allyl | |
| 203 | 1-methoxyethyl | H | n-propyl | (E)—3-chloro-2-propenyl | |
| 204 | 1-methoxyethyl | H | n-propyl | (E)—2-butenyl | |
| 205 | 2-methylthioethyl | H | methyl | ethyl | |
| 206 | 2-methylthioethyl | H | methyl | allyl | |
| 207 | 2-methylthioethyl | H | methyl | (E)—3-chloro-2-propenyl | |
| 208 | 2-methylthioethyl | H | methyl | (E)—2-butenyl | |
| 209 | 2-methylthioethyl | H | ethyl | ethyl | |
| 210 | 2-methylthioethyl | H | ethyl | allyl | |
| 211 | 2-methylthioethyl | H | ethyl | (E)—3-chloro-2-propenyl | |
| 212 | 2-methylthioethyl | H | ethyl | (E)—2-butenyl | |
| 213 | 2-methylthioethyl | H | n-propyl | ethyl | |
| 214 | 2-methylthioethyl | H | n-propyl | allyl | |
| 215 | 2-methylthioethyl | H | n-propyl | (E)—3-chloro-2-propenyl | |
| 216 | 2-methylthioethyl | H | n-propyl | (E)—2-butenyl | |
| 217 | 1,3-dimethoxypropyl | H | methyl | ethyl | |
| 218 | 1,3-eimethoxypropyl | H | methyl | allyl | |
| 219 | 1,3-dimethoxypropyl | H | methyl | (E)—3-chloro-2-propényl | |
| 220 | 1,3-dimethoxypropyl | H | methyl | (E)—2-butenyl | |
| 221 | 1,3-dimethoxypropyl | H | ethyl | ethyl | |
| 222 | 1,3-dimethoxypropyl | H | ethyl | allyl | |
| 223 | 1,3-dimethoxypropyl | H | ethyl | (E)—3-chloro-2-propenyl | |
| 224 | 1,3-dimethoxypropyl | H | ethyl | (E)—2-butenyl | |
| 225 | 1,3-dimethoxypropyl | H | n-propyl | ethyl | |
| 226 | 1,3-dimethoxypropyl | H | n-propyl | allyl | |
| 227 | 1,3-dimethoxypropyl | H | n-propyl | (E)—3-chloro-2-propenyl | |
| 228 | 1,3-dimethoxypropyl | H | n-propyl | (E)—2-butenyl | |
| 229 | 2-ethoxyethyl | H | methyl | ethyl | |
| 230 | 2-ethoxyethyl | H | methyl | allyl | |
| 231 | 2-ethoxyethyl | H | methyl | (E)—3-chloro-2-propenyl | |
| 232 | 2-ethoxyethyl | H | methyl | (E)—2-butenyl | |
| 233 | 2-ethoxyethyl | H | ethyl | ethyl | |
| 234 | 2-ethoxyethyl | H | ethyl | allyl | |
| 235 | 2-ethoxyethyl | H | ethyl | (E)—3-chloro-2-propenyl | |
| 236 | 2-ethoxyethyl | H | ethyl | (E)—2-butenyl | |
| 237 | 2-ethoxyethyl | H | n-propyl | ethyl | |
| 238 | 2-ethoxyethyl | H | n-propyl | allyl | |
| 239 | 2-ethoxyethyl | H | n-propyl | (E)—3-chloro-2-propenyl | |
| 240 | 2-ethoxyethyl | H | n-propyl | (E)—2-butenyl | |
| 241 | 1-methyl-2-methyl-thioethyl | H | methyl | ethyl | |
| 242 | 1-methyl-2-methyl-thioethyl | H | methyl | allyl | |
| 243 | 1-methyl-2-methyl-thioethyl | H | methyl | (E)—3-chloro-2-propenyl | |
| 244 | 1-methyl-2-methyl-thioethyl | H | methyl | (E)—2-butenyl | |
| 245 | 1-methyl-2-methyl-thioethyl | H | ethyl | ethyl | |
| 246 | 1-methyl-2-methyl-thioethyl | H | ethyl | allyl | |
| 247 | 1-methyl-2-methyl-thioethyl | H | ethyl | (E)—3-chloro-2-propenyl | |
| 248 | 1-methyl-2-methyl-thioethyl | H | ethyl | (E)—2-butenyl | |
| 249 | 1-methyl-2-methyl- | H | n-propyl | ethyl | |

TABLE 1-continued

List of active ingredients

| | R⁴ | R³ | R² | R¹ | Mp/°C. |
|---|---|---|---|---|---|
| | thioethyl | | | | |
| 250 | 1-methyl-2-methyl-thioethyl | H | n-propyl | allyl | |
| 251 | 1-methyl-2-methyl-thioethyl | H | n-propyl | (E)—3-chloro-2-propenyl | |
| 252 | 1-methyl-2-methyl-thioethyl | H | n-propyl | (E)—2-butenyl | |
| 253 | 2-methyl-1-methyl-thiomethyl-propyl | H | methyl | ethyl | |
| 254 | 2-methyl-1-methyl-thiomethyl-propyl | H | methyl | allyl | |
| 255 | 2-methyl-1-methyl-thiomethyl-propyl | H | methyl | (E)—3-chloro-2-propenyl | |
| 256 | 2-methyl-1-methyl-thiomethyl-propyl | H | methyl | (E)—2-butenyl | |
| 257 | 2-methyl-1-methyl-thiomethyl-propyl | H | ethyl | ethyl | |
| 258 | 2-methyl-1-methyl-thiomethyl-propyl | H | ethyl | allyl | |
| 259 | 2-methyl-1-methyl-thiomethyl-propyl | H | ethyl | (E)—3-chloro-2-propenyl | |
| 260 | 2-methyl-1-methyl-thiomethyl-propyl | H | ethyl | (E)—2-butenyl | |
| 261 | 2-methyl-1-methyl-thiomethyl-propyl | H | n-propyl | ethyl | |
| 262 | 2-methyl-1-methyl-thiomethyl-propyl | H | n-propyl | allyl | |
| 263 | 2-methyl-1-methyl-thiomethyl-propyl | H | n-propyl | (E)—3-chloro-2-propenyl | |
| 264 | 2-methyl-1-methyl-thiomethyl-propyl | H | n-propyl | (E)—2-butenyl | |
| 265 | 1-methylthio-methyl-butyl | H | methyl | ethyl | |
| 266 | 1-methylthio-methyl-butyl | H | methyl | allyl | |
| 267 | 1-methylthio-methyl-butyl | H | methyl | (E)—3-chloro-2-propenyl | |
| 268 | 1-methylthio-methyl-butyl | H | methyl | (E)—2-butenyl | |
| 269 | 1-methylthio-methyl-butyl | H | ethyl | ethyl | |
| 270 | 1-methylthio-methyl-butyl | H | ethyl | allyl | |
| 271 | 1-methylthio-methyl-butyl | H | ethyl | (E)—3-chloro-2-propenyl | |
| 272 | 1-methylthio-methyl-butyl | H | ethyl | (E)—2-butenyl | |
| 273 | 1-methylthio-methyl-butyl | H | n-propyl | ethyl | |
| 274 | 1-methylthio-methyl-butyl | H | n-propyl | allyl | |
| 275 | 1-methylthio-methyl-butyl | H | n-propyl | (E)—3-chloro-2-propenyl | |
| 276 | 1-methylthio-methyl-butyl | H | n-propyl | (E)—2-butenyl | |
| 277 | 2-methyl-1-propenyl | H | methyl | ethyl | |
| 278 | 2-methyl-1-propenyl | H | methyl | allyl | |
| 279 | 2-methyl-1-propenyl | H | methyl | (E)—3-chloro-2-propenyl | |
| 280 | 2-methyl-1-propenyl | H | methyl | (E)—2-butenyl | |
| 281 | 2-methyl-1-propenyl | H | ethyl | ethyl | |
| 282 | 2-methyl-1-propenyl | H | ethyl | allyl | |
| 283 | 2-methyl-1-propenyl | H | ethyl | (E)—3-chloro-2-propenyl | |
| 284 | 2-methyl-1-propenyl | H | ethyl | (E)—2-butenyl | |
| 285 | 2-methyl-1-propenyl | H | n-propyl | ethyl | |
| 286 | 2-methyl-1-propenyl | H | n-propyl | allyl | |
| 287 | 2-methyl-1-propenyl | H | n-propyl | (E)—3-chloro-2-propenyl | |
| 288 | 2-methyl-1-propenyl | H | n-propyl | (E)—2-butenyl | |
| 289 | methoxymethyl | H | n-propyl | 3-methyl-5-isoxazolylmethyl | |
| 290 | methoxymethyl | H | n-propyl | 5-chloro-3-thenyl | |
| 291 | methoxymethyl | H | n-propyl | 3-thenyl | |
| 292 | i-propyl | H | ethyl | 5-chloro-2-thenyl | 80–84 |
| 293 | i-propyl | H | ethyl | 5-bromo-2-thenyl | 79–84 |
| 294 | i-propyl | H | n-propyl | 5-chloro-2-thenyl | 82–87 |
| 295 | i-propyl | H | n-propyl | 5-bromo-2-thenyl | 86–90 |
| 296 | i-propyl | H | n-propyl | 3-chlorobenzyl | 72–74 |
| 297 | i-propyl | H | n-propyl | 4-cyanobenzyl | 108–112 |
| 298 | i-propyl | H | n-propyl | 3-methyl-5-isoxazolylmethyl | 76–79 |
| 299 | i-propyl | H | n-propyl | 3,3-dichlorocyclopropylmethyl | 89–91 |
| 300 | i-propyl | H | n-propyl | 4-chloro-benzyl | 113–114 |
| 301 | i-propyl | H | n-propyl | 3-trifluoromethylbenzyl | 122–123 |

TABLE 1-continued

List of active ingredients

| | R⁴ | R³ | R² | R¹ | Mp/°C. |
|---|---|---|---|---|---|
| 302 | i-propyl | H | ethyl | 4-chlorobenzyl | 106–109 |
| 303 | i-propyl | H | ethyl | 3-trifluoromethylbenzyl | 75–76 |
| 304 | t-butyl | H | n-propyl | 2-chlorophenetyl | oil |
| 305 | ethyl | H | ethyl | 2-chlorophenetyl | oil |
| 306 | i-propyl | H | ethyl | 2-chlorphenetyl | oil |
| 307 | i-propyl | H | methyl | 2-chlorophenetyl | oil |
| 308 | 1-methoxyethyl | benzoyl | n-propyl | ethyl | oil |
| 309 | 1-methoxyethyl | propionyl | n-propyl | ethyl | oil |
| 310 | 1-methoxyethyl | butyryl | n-propyl | ethyl | oil |
| 311 | 1-methoxyethyl | pivaloyl | n-propyl | ethyl | oil |
| 312 | 2,6-dimethylheptyl | propionyl | ethyl | allyl | oil |
| 313 | 2,6-dimethylheptyl | propionyl | ethyl | allyl | oil |
| 314 | 2,6-dimethylheptyl | benzoyl | ethyl | allyl | oil |
| 315 | 2,6-dimethylheptyl | pivaloyl | ethyl | allyl | oil |
| 316 | 2,6-dimethylheptyl | butyryl | n-propyl | ethyl | oil |
| 317 | 2,6-dimethylheptyl | propionyl | n-propyl | ethyl | oil |
| 318 | 2,6-dimethylheptyl | benzoyl | n-propyl | ethyl | oil |
| 319 | 2,6-dimethylheptyl | palmitoyl | n-propyl | ethyl | oil |
| 320 | 1-methoxyethyl | butyryl | ethyl | allyl | oil |
| 321 | 1-methoxyethyl | benzoyl | ethyl | allyl | oil |
| 322 | 1-methoxyethyl | pivaloyl | ethyl | allyl | oil |
| 323 | 1-methoxyethyl | palmitoyl | ethyl | allyl | oil |
| 324 | 1-methoxyethoxyethyl | H | n-propyl | ethyl | |
| 325 | 1-methoxyethoxyethyl | H | n-propyl | allyl | |
| 326 | 1-methoxyethoxyethyl | H | n-propyl | (E)—2-butenyl | |
| 327 | 1-methoxyethoxyethyl | H | n-propyl | (E)—3-chloro-2-propenyl | |
| 328 | 1-methoxymethyl-ethyl | H | ethyl | ethyl | |
| 329 | 1-methoxymethyl-ethyl | H | ethyl | allyl | |
| 330 | 1-methoxymethyl-ethyl | H | ethyl | (E)—2-butenyl | |
| 331 | 1-methoxymethyl-ethyl | H | ethyl | (E)—3-chloro-2-propenyl | |
| 332 | 1-methoxymethyl-ethyl | H | n-propyl | ethyl | |
| 333 | 1-methoxymethyl-ethyl | H | n-propyl | allyl | |
| 334 | 1-methoxymethyl-ethyl | H | n-Propyl | (E)—2-butenyl | |
| 335 | 1-methoxymethyl-ethyl | H | n-propyl | (E)—3-chloro-2-propenyl | |
| 336 | i-propyl | butyryl | ethyl | (E)—2-butenyl | oil |
| 337 | i-propyl | pivaloyl | ethyl | (E)—2-butenyl | oil |
| 338 | i-propyl | benzoyl | ethyl | (E)—2-butenyl | oil |
| 339 | i-propyl | butyryl | ethyl | ethyl | oil |
| 341 | i-propyl | pivaloyl | ethyl | ethyl | oil |
| 342 | i-propyl | propionyl | ethyl | (E)—3-chloro-2-propenyl | oil |
| 343 | i-propyl | pivaloyl | ethyl | (E)—3-chloro-2-propenyl | oil |
| 344 | i-propyl | Na | ethyl | ethyl | |
| 345 | i-propyl | NH₄ | ethyl | ethyl | |
| 346 | i-propyl | ½ Fe | ethyl | ethyl | |
| 347 | i-propyl | ½ Mg | ethyl | ethyl | |

TABLE 2

Elemental analyses and ¹H—NMR data of selected active ingredients

| Active ingredient No. | Elemental analysis | | | | | | ¹H—NMR data |
|---|---|---|---|---|---|---|---|
| | C | H | N | S | Cl | Br | |
| 5 | | | | | | | 1.16 (t,3H), 1.26 (t,3H), 1.34 (t, 3H), 2.68 (q, ZH), 4.13 (q,2H), 5.92 (s, 1H) |
| 6 | | | | | | | 1.16 (t,3H), 1.28 (t,3H), 2.78 (q,2H), 4.56 (d,2H), 5.92 (s,1H) |
| 7 | | | | | | | 1.13 (t,3H), 1.25 (t,3H), 2.66 (q,2H), 4.52 (d,2H), 5.9 (s, 1H), 6.35 (d,1H) |
| 8 | | | | | | | 1.13 (t,3H), 1.26 (t,3H), 1.78 (d,3H), 2.68 (q,2H), 4.45 (d,2H), 5.9 (s,1H) |
| 9 | | | | | | | 0.96 (t,3H), 1.24 (t,3H), 1.3 (t,3H), 1.54 ("6",2H), 4.1 (q,2H), 5.92 (s,1H) |
| 10 | | | | | | | 0.96 (t,3H), 1.24 (t, 3H), 1.54 ("6",2H), 2.65 (q,2H), 4.52 (d,2H), 5.9 (s,1H) |
| 11 | | | | | | | 0.95 (t,3H), 1.25 (t,3H), 2.65 (q,2H), 4.5 (d,2H), 5.92 (s,1H), 6.08 (dt,1H), 6.35 (d,1H) |
| 12 | | | | | | | 0.95 (t,3H), 1.25 (t,3H), 1.54 ("6",2H), 1.75 (d,3H), 2.65 (q,2H), 4.45 (d,2H), 5.92 (s,1H) |
| 17 | | | | | | | 0.97 (t,3H), 1.13 (t,3H), 1.34 (t,3H), 1.67 ("6",2H), 2.6 (t,2H), 4.12 (q,2H), 5.9 (s,1H) |
| 18 | | | | | | | 0.97 (t,3H), 1.14 (t,3H), 1.67 ("6",2H), 2.6 (t,2H), 4.53 (d,2H), 5.36 (dd,2H), 5.9 (s,1H) |

TABLE 2-continued
Elemental analyses and $^1$H—NMR data of selected active ingredients

| Active ingredient No. | Elemental analysis | | | | | | $^1$H—NMR data |
|---|---|---|---|---|---|---|---|
| | | C | H | N | S | Cl | Br | |
| 19 | | | | | | | | 0.97 (t,3H), 1.13 (t,3H), 166 ("6",2H), 4.52 ((d,2H), 5.9 (s,1H), 6.35 (d,1H) |
| 20 | | | | | | | | 0.97 (t,3H), 1.14 (t,3H), 2.6 (t,2H), 4.47 (d,2H), 5.9 (s,1H) |
| 21 | | | | | | | | 0.96 (t,6H), 1.14 (t,3H), 2.6 (t,2H, 4.11 (q,2H), 5.92 (s,1H) |
| 22 | | | | | | | | 0.96 (t,6H), 1.54 ("6",2H), 1.67 ("6",2H), 2.59 (t,2H), 4.53 (d, 2H), 5.9 (s,1H) |
| 23 | | | | | | | | 0.95 (t,3H), 0.97 (t,3H), 1.53 ("6",2H), 1.69 ("6",2H), 2.6 (t,2H), 4.53 (d,2H), 5.92 (s,1H), 6.1 (dt,1H), 6.36 (d, 1H) |
| 24 | | | | | | | | 0.96 (t,6H), 1.54 ("6",2H), 1.67 ("6",2H), 1.73 (d,3H), 2.6 (t,2H), 4.45 (d,2H), 5,91 (s,1H) |
| 25 | | | | | | | | 1.3 (d,6H), 2.34 (s,3H), 4.1 (q,2H), 5.9 (s,1H) |
| 26 | | | | | | | | 1.27 (d,6H), 2.39 (s,3H), 4.55 (d,2H), 5.92 (s,1H) |
| 27 | | | | | | | | 1.28 (d,6H), 2.32 (s,3H), 4.52 (d,2H), 5.93 (s,1H), 6.34 (d,1H) |
| 28 | calc. | 65.0 | 7.3 | 8.4 | | | | 1.25 (d,6H), 1.76 (d,3H), 2.4 (s,3H) |
| | found | 64.6 | 7.3 | 8.7 | | | | 4.47 (d,2H), 5.9 (s,1H) |
| 29 | calc. | 63.7 | 7.8 | 8.8 | | | | 1.15 (t,3H), 1.25 (d,6H), 1.3 (t,3H) |
| | found | 63.2 | 7.5 | 8.8 | | | | 4.1 (q,2H), 5.92 (s,1H) |
| 30 | calc. | 65.0 | 7.3 | 8.4 | | | | 1.13 (t,3H), 1.25 (d,6H), 4.53 (d,2H) |
| | found | 64.8 | 7.3 | 8.7 | | | | 5.92 (s,1H), |
| 31 | calc. | 58.9 | 6.3 | 7.6 | | 9.7 | | 1.12 (t,3H), 1.26 (d,6H), 4.5 (d,2H) |
| | found | 59.1 | 6.2 | 7.7 | | 9.3 | | 5.91 (s,1H) |
| 32 | calc. | 65.9 | 7.6 | 8.1 | | | | 1.15 (t,3H), 1.28 (d,6H), 1.78 (d,3H) |
| | found | 65.5 | 7.2 | 8.4 | | | | 4.45 (d,2H), 5.93 (s,1H) |
| 33 | calc. | 64.7 | 7.8 | 8.4 | | | | 0.96 (t,3H), 1.27 (d,6H), 1.3 (t,3H) |
| | found | 64.3 | 7.7 | 8.5 | | | | 1.55 ("6",2H). 4.1 (q,2H), 6.94 (s,1H) |
| 34 | calc. | 65.9 | 7.6 | 8.1 | | | | 0.96 (t,3H), 1.28 (d,6H), 1.54 ("6",2H), |
| | found | 64.4 | 7.5 | 8.7 | | | | 4.52 (d,2H), 5.92 (s,1H) |
| 35 | calc. | 59.9 | 6.6 | 7.4 | | 9.3 | | 0.96 (t,3H), 1.27 (d,6H), 1.53 ("6"),2H), |
| | found | 59.3 | 6.5 | 7.6 | | 9.2 | | 4.53 (d,2H), 5.92 (s,1H) |
| 36 | calc. | 66.6 | 7.8 | 7.8 | | | | 0.97 (t,3H), 1.27 (d,6H), 1.53 ("6",2H) |
| | found | 66.3 | 7.6 | 7.6 | | | | 1.76 (d,3H), 4.42 (d,2H), 5.91 (s,1H) |
| 37 | | | | | | | | 0.97 (t,3H), 1.37 (t,3H), 1.67 ("5",2H), 2.45 (s,3H), 2.68 (t,2H), 4.17 (q,2H), 5.9 (s,1H) |
| 38 | | | | | | | | 0.96 (t,3H), 1.42 ("6",2H), 1.67 ("5",2H), 2.42 (s,3H), 2.67 (t,2H), 4.59 (d,2H), 5.9 (s,1H), 6.4 (d,1H) |
| 39 | | | | | | | | 0.97 (t,3H), 1.42 ("6",2H), 1.67 ("5",2H), 2.34 (s,3H), 2.67 (t,2H), 4.6 (d,2H), 5.97 (s,1H), 6.4 (d,1H) |
| 40 | | | | | | | | 0.96 (t,3H), 1.41 ("6",2H), 1.66 ("5",2H), 1.8 (d,3H), 2.42 (s,3H), 2.66 (t,2H), 4.48 (d,2H), 5.93 (s,1H) |
| 41 | | | | | | | | 0.94 (t,3H), 1.15 (t,3H), 1.33 (t,3H), 1.63 ("5",2H), 2.63 (t,2H), 4.12 (q,2H), 5.91 (s,1H) |
| 42 | | | | | | | | 0.94 (t,3H), 4.53 (d,2H), 5.34 (dd,2H), 5.9 (s,1H) |
| 43 | | | | | | | | 0.94 (t,3H), 1.12 (t,3H), 1.38 ("6", 2H), 1.64 ("5",2H), 2.63 (t,2H), 4.52 (d,2H), 5.9 (s,1H), 6.35 (d, 1H) |
| 44 | | | | | | | | 0.93 (t,3H), 1.14 (t,3H), 1.38 ("6",2H), 1.61 ("5",2H), 1.77 (d,3H), 2.63 (t,2H), 4.46 (d,2H), 5.89 (s,1H) |
| 45 | | | | | | | | 0.8 (t,3H), 0.88 (t,3H), 3.88 (q,2H), 4.02 (q,2H), 6.21 (s,1H) |
| 46 | | | | | | | | 0.82 (t,3H), 0.88 (t,3H), 4.5 (d,2H), 6.21 (s,1H) |
| 48 | | | | | | | | 0.84 (t,3H), 0.92 (t,3H), 1.7 (d,3H), 6.24 (s,1H) |
| 53 | | | | | | | | 0.9 (t,3H), 1.15 (t,3H), 1.25 (d,3H), 1.32 (t,3H), 4.15 (q,2H), 5.92 (s,1H) |
| 54 | | | | | | | | 0.89 (t,3H), 1.15 (t,3H), 1.25 (d,3H), 4.56 (d,2H), 5.91 (s,1H) |
| 55 | | | | | | | | 0.9 (t,3H), 1.13 (t,3H), 1.25 (d,3H), 4.56 (d,2H), 5.92 (s,1H), 6.12 (dt,1H), 6.38 (d,1H) |
| 56 | | | | | | | | 0.9 (t,3H), 1.15 (t,3H), 1.25 (d,3H), 1.78 (d,3H), 4.48 (d,2H), 5.91 (s,1H) |
| 57 | | | | | | | | 0.89 (t,3H), 0.96 (t,3H), 1.24 (d,3H), 1.34 (t,3H), 4.12 (q,2H), 5.9 (s,1H) |

TABLE 2-continued

Elemental analyses and $^1$H—NMR data of selected active ingredients

| Active ingredient No. | Elemental analysis | | | | | | $^1$H—NMR data |
|---|---|---|---|---|---|---|---|
| | C | H | N | S | Cl | Br | |
| 58 | | | | | | | 0.88 (t,3H), 0.96 (t,3H), 1.23 (d,3H), 4.54 (d,2H), 5.34 (dd,2H), 5.92 (s,1H) |
| 59 | | | | | | | 0.88 (t,3H), 0.95 (t,3H), 1.23 (d,3H), 4.53 (d,2H), 5.9 (s,1H), 6.1 (dt, 1H), 6.36 (d,1H) |
| 60 | | | | | | | 0.9 (t,3H), 0.95 (t,3H), 1.24 (d,3H), 1.7 (d,3H), 4.43 (d,2H), 5.89 (s,1H) |
| 65 | | | | | | | 1.13 (t,3H), 1.3 (s,9H), 4.1 (q,2H), 5.95 (s, 1H) |
| 66 | | | | | | | 1.16 (t,3H), 1.34 (s,9H), 4.55 (d,2H), 5.9 (s,1H) |
| 67 | | | | | | | 1.1 (t,3H), 1.3 (s,9H), 4.53 (d,2H), 5.93 (s,1H), 6.35 (d,1H) |
| 68 | | | | | | | 1.12 (t,3H), 1.3 (s,9H), 1.77 (d,3H), 4.45 (d,2H), 5.92 (s,1H) |
| 69 | | | | | | | 0.95 (t,3H), 1.32 (s,9H), 1.53 ("6"),ZH, 4.1 (q,2H), 5.97 (s,1H) |
| 70 | | | | | | | 0.96 (t,3H), 1.3 (s,9H), 4.53 (d,2H), 5.92 (s, 1H) |
| 71 | | | | | | | 0.95 (t,3H), 1.3 (s,9H), 1.5 ("6", 2H), 4.52 (d,2H), 5.94 (s, 1H), 6.35 (d, 1H) |
| 72 | | | | | | | 0.95 (t,3H), 1.3 (s,9H), 1.77 (d,3H) 4.44 (d,2H), 5.93 (s,1H) |
| 77 | | | | | | | 0.97 (d,6H), 1.17 (t,3H), 1.34 (t,3H), 2.53 (d,2H), 4.14 (q,2H), 5.9 (s,1H) |
| 78 | | | | | | | 0.98 (d,6H), 1.17 (t,3H), 2.54 (d,2H), 4.57 (d,2H), 5.4 (dd,2H), 5.9 (s,1H) |
| 79 | | | | | | | 0.95 (d,6H), 1.13 (t,3H), 2.51 (d,2H), 4.52 (d,2H), 5.9 (s,1H), 6.1 (dt,1H), 6.35 (d, 1H) |
| 80 | | | | | | | 0.95 (d,6H), 1.14 (t,3H), 1.77 (d,3H), 2.5 (d,2H), 4.46 (d,2H), 5.88 (s,1H) |
| 81 | | | | | | | 0.96 (d,6H), 1.32 (t,3H), 1.55 ("6",ZH), 2.5 (d,2H), 4.11 (q,2H), 5.88 (s,1H) |
| 82 | | | | | | | 0.95 (d,6H), 0.97 (t,3H), 1.54 ("6",2H), 1.95 ("7",2H), 2.5 (d,2H), 4.54 (d,2H), 5.9 (s, 1H) |
| 83 | | | | | | | 0.95 (d,6H), 1.52 ("6",2H), 1.95 ("7",2H), 2.5 (d,2H), 4.53 (d,2H), 5,9 (s,1H), 6.1 (dt,1H), 6.36 (d,1H) |
| 84 | | | | | | | 0.94 (d,6H), 1.54 ("6",2H), 1.77 (d,3H), 1.95 ("7",2H), 2.5 (d,2H), 4.45 (d,2H), 5.87 (s,1H) |
| 89 | | | | | | | 0.88 (s,9H), 0.98 (d,3H), 1.16 (t,3H), 1.34 (t,3H), 4.12 (q, 2H), 5.9 (s,1H) |
| 90 | | | | | | | 1.34 (t,3H), 4.12 (q, 2H), 5.9 (s,1H) 0.87 (s,9H), 0.97 (d,3H), 1.16 (t,3H), 4.55 (d,2H), 5.89 (s,1H) |
| 91 | | | | | | | 0.87 (s,9H), 0.96 (d,3H), 1.13 (t,3H), 4.52 (d,2H), 5.9 (s,1H), 6.1 (dt,1H), 6.35 (d,1H) |
| 92 | | | | | | | 0.87 (s,9H), 0.97 (d,3H), 1.17 (t,3H), 1.77 (d,3H), 4.47 (d,2H), 5.88 (s,1H) |
| 93 | | | | | | | 0.87 (s,9H), 0.97 (d,3H), 1.32 (t,2H), 4.12 (q,2H), 5.88 (s,1H) |
| 94 | | | | | | | 0.87 (s,9H), 0.97 (d,3H), 0.99 (t,3H), 4.53 (d,2H), 5.89 (s,1H) |
| 95 | | | | | | | 0.87 (s,9H), 0.96 (d,3H), 4.53 (d,2H), 5.9 (s,1H), 6.35 (d,1H) |
| 96 | | | | | | | 0.87 (s,9H), 0.96 (d,3H), 1.77 (d,3H), 4.44 (d,2H), 5.88 (s,1H) |
| 105 | | | | | | | 0.84 (t,3H), 0.87 (t,3H), 1.14 (t,3H), 1.33 (t,3H), 4.12 (q,2H), 5.88 (s,1H) |
| 106 | | | | | | | 0.83 (t,3H), 0.86 (t,3H), 1.14 (t,3H), 4.56 (d,2H), 5.87 (s,1H) |
| 107 | | | | | | | 0.84 (t,3H), 0.87 (t,3H), 1.12 (t,3H), 4.55 (d,2H), 5.88 (s,1H), 6.11 (dt,1H), 6.37 (d,1H) |
| 108 | | | | | | | 0.83 (t,3H), 0.86 (t,3H), 1.14 (t,3H), 1.78 (d,3H), 4.48 (d,2H), 6.88 (s,1H) |
| 113 | | | | | | | 0.85 (d,6H), 0.87 (t,3H), 1.14 (t,3H), 1.35 (t,3H), 4.12 (q,2H), 5.9 (s,1H) |
| 114 | | | | | | | 0.85 (d,6H), 0.87 (t,3H), 1.15 (t,3H), 4.55 (d,2H), 5.89 (s,1H) |
| 115 | | | | | | | 0.85 (d,6H), 0.87 (t,3H), 4.53 (d,2H), 5.89 (s,1H), 6.36 (d,1H) |
| 116 | | | | | | | 0.86 (d,6H), 0.9 (t,3H), 1.15 (t,3H), 1.78 (d,3H), 4.48 (d,2H), 5.9 (s,1H) |

TABLE 2-continued

Elemental analyses and $^1$H—NMR data of selected active ingredients

| Active ingredient No. | | Elemental analysis | | | | | | $^1$H—NMR data |
|---|---|---|---|---|---|---|---|---|
| | | C | H | N | S | Cl | Br | |
| 117 | | | | | | | | 0.85 (d,6H), 0.87 (t,3H), 1.34 (t,3H), 4.13 (q,2H), 5.9 (s,1H) |
| 118 | | | | | | | | 0.85 (d,6H), 0.87 (t,3H), 4.52 (d,2H), 5.36 (dd,2H), 5.89 (s,1H) |
| 119 | | | | | | | | 0.87 (d,6H), 0.95 (t,3H), 4.53 (d,2H), 5.9 (s,1H), 6.1 (dt,1H), 6.38 (d,1H) |
| 120 | | | | | | | | 0.85 (d,6H), 0.87(t,3H), 0.95 (t,3H) 1.76 (d,3H), 4.45 (d,2H), 5.88 (s,1H) |
| 137 | | | | | | | | 1.14 (t,3H), 1.35 (t,3H), 4.1 (q,2H), 5.9 (s,1H) |
| 138 | | | | | | | | 1.14 (t,3H), 4.54 (d,2H), 5.35 (dd,2H), 5.9 (s,1H) |
| 139 | | | | | | | | 1.12 (t,3H), 4.52 (d,2H), 5.9 (s,1H), 6.1 (dt,1H), 6.35 (d,1H) |
| 140 | | | | | | | | 1.13 (t,3H), 1.75 (d,3H), 4.45 (d,2H), 5.88 (s,1H) |
| 141 | | | | | | | | 0.96 (t,3H), 1.32 (t,3H), 4.1 (q,2H), 5.9 (s,1H) |
| 142 | | | | | | | | 0.95 (t,3H), 1.55 ("6",2H), 4.54 (d,2H), 5.36 (dd,2H), 5.9 (s,1H) |
| 143 | | | | | | | | 0.95 (t,3H), 4.52 (d,2H), 5.9 (s,1H), 6.1 (dt,1H), 6.35 (d,1H) |
| 144 | | | | | | | | 0.96 (t,3H), 1.54 ("6",2H), 1,75 (d,3H), 4.44 (d,2H), 5.88 (s,1H) |
| 153 | calc. | 60.7 | 7.2 | 8.3 | | | | 0.95 (t,3H), 1.31 (6,3H), 1.53 ("6",2H) |
| | found | 61.1 | 7.2 | 8.2 | | | | 3.39 (s,3H), 4.12 (q,2H), 4.5 (s,2H), 6.1 (s,1H), 6,12 (s,1H) |
| 154 | calc | 62.1 | 6.9 | 8.0 | | | | 0.96 (t,3H), 1.54 ("6",2H), 3.4 (s,3H) |
| | found | 62.5 | 7.1 | 8.0 | | | | 4.5 (s,2H), 4.54 (d,2H), 6.15 (s,1H) |
| 155 | calc. | 56.5 | 6.1 | 7.3 | | 9.3 | | 0.94 (t,3H), 1.5 ("6",2H), 3.4 (s,3H), |
| | found | 57.7 | 6.1 | 6.9 | | 7.4 | | 4.5 (s,2H), 4.52 (d,2H), 6.13 (s,1H) |
| 156 | calc. | 63.0 | 7.2 | 7.7 | | | | 0.97 (t,3H), 1.55 ("6",2H), 1.68 (d,3H), |
| | found | 57.7 | 6.1 | 6.9 | | | | 4.5 (s,2H), 4.52 (d,2H), 6.13 (s,1H) |
| 197 | | | | | | | | 1.13 (t,3H), 1.34 (t,3H), 1.47 (d,3H), 3.28 (2,3H), 4.13 (q, 2H), 4.5 (q, 1H), 6.1 (s, 1H) |
| 198 | | | | | | | | 1.13 (t,3H), 1.46 (d,3H), 3.27 (s,3H), 4.5 (q,1H), 4.55 (d,2H), 5.35 (dd,2H), 6.08 (s,1H) |
| 199 | | | | | | | | 1.13 (t,3H), 1.48 (d,3H), 3.28 (s,3H), 4.5 (q,1H), 4.55 (d,2H), 6.08 (s,1H), 6.35 (d,1H) |
| 200 | | | | | | | | 1.14 (t,3H), 1.47 (d,3H), 1.78 (s,3H), 3.28 (s,3H), 4.48 (d,2H), 4.5 (q,1H), 6.08 (s,1H) |
| 201 | | | | | | | | 0.97 (t,3H), 1.32 (t,3H), 1.47 (d,3H), 3.3 (s,3H), 4.12 (q,2H), 4.5 (q,1H), 6.08 (s,1H) |
| 202 | | | | | | | | 0.96 (t,3H), 1.47 (d,3H), 3.28 (s,3H), 4.5 (q,1H), 4.52 (d, 2H), 5.37 (dd,2H), 6.08 (s,1H) |
| 203 | | | | | | | | 0.96 (t,3H), 1.47 (d,3H), 3.3 (s,3H), 4.5 (d,2H), 6.08 (s,1H), 6.34 (d,1H) |
| 204 | | | | | | | | 0.97 (t,3H), 1.47 (d,3H), 1.77 (d,3H), 3.28 (s,3H), 4.45 (d,2H), 6.08 (s,1H) |
| 281 | | | | | | | | 1.15 (t,3H), 1.32 (t,3H), 1.94 (s,3H), 2.0 (s,3H), 4.12 (q,2H), 6.03 (s,1H), 6.08 (s,1H) |
| 282 | | | | | | | | 1.14 (t,3H), 1.94 (s,3H), 2.0 (s,3H), 4.53 (d,2H), 5.37 (dd,2H), 6.01 (s,1H), 6.08 (s,1H) |
| 283 | | | | | | | | 1.13 (t,3H), 1.93 (s,3H), 2.0 (s,3H), 4.53 (d,2H), 6.03 (s,1H), 6.07 (s,1H), 6.36 (d,1H) |
| 284 | | | | | | | | 1.14 (t,3H), 1.77 (d,3H), 1.93 (s,3H), 2.0 (s,3H), 4.45 (d,2H), 6.02 (s,1H), 6.08 (s,1H) |
| 285 | | | | | | | | 0.97 (t,3H), 1.33 (t,3H), 1.55 ("6",2H), 1.93 (s,3H), 2.0 (s,3H), 4.12 (q,2H), 6.02 (s,1H), 6.08 (s,1H) |
| 286 | | | | | | | | 0.96 (t,3H), 1.55 ("6",2H), 1.94 (s,3H), 2.0 (s,3H), 4.52 (d,2H), 5.36 (dd,2H), 6.0 (s,1H), 6.08 (s,1H) |
| 287 | | | | | | | | 0.94 (t,3H), 1.52 ("6",2H), 1.94 (s,3H), 2.0 (s,3H), 4.52 (d,2H), 6.02 (s,1H), 6,08 (s,1H), 6.35 (d,1H) |
| 288 | | | | | | | | 0.96 (t,3H), 1.52 ("6",2H), 1.77 (d,3H), 1.95 (s,3H), 1.99 (s,3H), 4.45 (d,2H), 6.0 (s,1H), 6.08 (s,1H) |

TABLE 2-continued

Elemental analyses and $^1$H—NMR data of selected active ingredients

| Active ingredient No. | | Elemental analysis | | | | | | $^1$H—NMR data |
|---|---|---|---|---|---|---|---|---|
| | | C | H | N | S | Cl | Br | |
| 289 | calc. | 59.5 | 6.3 | 10.4 | | | | 0.93 (t,3H), 1.5 ("6",2H), 2.33 (s,3H) |
| | found | 59.8 | 6.2 | 9.7 | | | | 3.4 (s,3H), 4.58 (s,2H), 5.1 (s,2H), |
| | | | | | | | | 6.14 (s,1H), 6.18 (s,1H) |
| 290 | calc. | 54.7 | 5.3 | 6.4 | 7.3 | 8.1 | | 0.95 (t,3H), 1.5 ("6",2H), 3.4 (s,3H) |
| | found | 54.8 | 5.4 | 6.4 | 8.3 | 7.7 | | 4.48 (s,2H), 4.93 (s,2H), 6.1 (s,1H), |
| | | | | | | | | 6.9 (d,1H), 7.08 (d,1H) |
| 291 | calc. | 59.4 | 6.0 | 6.9 | 7.9 | | | 0.95 (t,3H), 1.5 ("6",2H), 3.38 (s,3H), |
| | found | 59.9 | 6.3 | 6.9 | 7.3 | | | 4.48 (s,2H), 5.08 (s,2H), 6.1 (s,1H) |
| 292 | calc. | 56.8 | 5.5 | 6.6 | 7.6 | 8.4 | | 1.12 (t,3H), 1.28 (d,6H), 5.1 (s,2H), |
| | found | 56.5 | 5.4 | 7.2 | 7.6 | 8.8 | | 5.92 (s,1H), 6.84 (d,1H), 6.87 (d,1H), |
| 293 | calc. | 51.4 | 4.9 | 6.0 | 6.9 | | 17.1 | 1.1 (t,3H), 1.27 (d,6H), 5.13 (s,2H), |
| | found | 51.8 | 5.0 | 6.6 | 6.5 | | 15.8 | 5.92 (s,1H), 6.85 (d,1H), 6.95 (d,1H), |
| 294 | calc. | 57.7 | 5.8 | 6.4 | 7.3 | 8.1 | | 0.93 (t,3H), 1.24 (d,6H), 5.1 (s,2H), |
| | found | 57.4 | 5.7 | 7.4 | 7.0 | 7.8 | | 5.95 (s,1H), 6.8 (d,1H), 6.86 (d,1H) |
| 295 | calc. | 52.4 | 5.2 | 5.8 | 6.7 | | 16.6 | 0.92 (t,3H), 1.27 (d,6H), 5.12 (s,2H), |
| | found | 51.7 | 5.2 | 6.2 | 6.9 | | 16.6 | 5.93 (s,1H), 6.85 (d,1H), 6.95 (d,1H) |
| 296 | calc. | 64.1 | 6.3 | 6.5 | | 8.2 | | 0.95 (t,3H), 1.25 (d,6H), 5.02 (s,2H), |
| | found | 63.8 | 6.4 | 6.9 | | 8.6 | | 5.95 (s,1H), 7.05–7,4 (m,4H) |
| 297 | calc. | 68.4 | 6.5 | 10.0 | | | | 0.95 (t,3H), 1.26 (d,6H), 5.13 (s,2H), |
| | found | 68.0 | 6.5 | 10.1 | | | | 5.95 (s,1H), 7.56 (AA'BB',4H) |
| 298 | calc. | 62.8 | 6.8 | 10.5 | | | | 0.78 (t,3H), 1.2 (d,6H), 2.23 (s,3H), |
| | found | 62.3 | 6.7 | 10.8 | | | | 2.35 (t,2H), 5.1 (s,2H), 6.25 (s,1H), |
| | | | | | | | | 6.35 (s,1H) |
| 299 | calc. | 56.0 | 6.1 | 6.5 | | 16.5 | | 0.98 (t,3H), 1.25 (d,6H), 1.55 ("q", 2H), |
| | found | 55.4 | 6.2 | 6.9 | | 16.9 | | 4.2 (d,2H), 5.93 (s,1H) |
| 300 | | | | | | | | 0.94 (t,3H), 1.25 (d,6H), 1.52 ("6",2H), |
| | | | | | | | | 5.0 (s,2H), 5.9 (s,1H), 7.32 (aa'bb',4H) |
| 301 | | | | | | | | 0.94 (t,3H), 1.25 (d,6H), 1.52 ("6",2H), |
| | | | | | | | | 5.12 (s,2H), 5.9 (s,1H) |
| 302 | | | | | | | | 0.84 (t,3H), 1.17 (d,6H), 5.07 (s,2H), |
| | | | | | | | | 6.27 (s,1H) |
| 303 | | | | | | | | 0.88 (t,3H), 1.18 (d,6H), 5.17 (s,2H), |
| | | | | | | | | 6.26 (s,1H) |
| 304 | | | | | | | | 0.9 (t,3H), 1.31 (s,9H), 3.17 (t,2H), |
| | | | | | | | | 5.96 (s,1H) |
| 305 | | | | | | | | 1.04 (t,3H), 1.23 (t,3H), 2.64 (q,2H), |
| | | | | | | | | 3.12 (t,2H), 4.27 (t,2H), 5.92 (s,1H) |
| 306 | | | | | | | | 1.08 (t,3H), 1.28 (d,6H), 3.17 (t,2H), |
| | | | | | | | | 4.3 (t,2H), 5.93 (s,1H) |
| 307 | | | | | | | | 1.27 (d,6H), 2.33 (s,3H), 3.16 (t,2H), |
| | | | | | | | | 4.32 (t,2H), 5.93 (s,1H) |
| 308 | | | | | | | | 0.92 (t,3H), 1.12 (t,3H), 1.5 (d,3H), |
| | | | | | | | | 3.33 (s,3H), 4.0 (q,2H), 6.2 (s,1H), |
| | | | | | | | | 7.53 (t,2H), 7.7 (t,1H), 8.07 (d,2H) |
| 309 | | | | | | | | 0.98 (t,3H), 1.37 (t,3H), 1.5 (d,3H), |
| | | | | | | | | 3.34 (s,3H), 4.15 (q,2H), 6.12 (s,1H) |
| 310 | | | | | | | | 1.47 (d,3H), 3.28 (s,3H), 6.15 (s,1H) |
| 311 | | | | | | | | 0.9 (t,3H), 1.25 (s,9H), 1.47 (d,3H), |
| | | | | | | | | 3.3 (s,3H), 4.13 (q,2H), 4.5 (q,1H), |
| | | | | | | | | 6.16 (s,1H) |
| 312 | | | | | | | | 0.88 (d,6H), 4.57 (d,2H), 5.9 (s,1H) |
| 313 | | | | | | | | 0.88 (d,6H), 5.94 (s,1H) |
| 314 | | | | | | | | 8.88 (d,6H), 4.42 (d,2H), 5.98 (s,1H) |
| 315 | | | | | | | | 0.88 (d,6H), 1.25 (s,9H), 4.57 (d,2H), |
| | | | | | | | | 5.92 (s,1H) |
| 316 | | | | | | | | 0.88 (d,6H), 4.13 (q,2H), 5.94 (s,1H) |
| 317 | | | | | | | | 0.88 (d,6H), 0.92 (t,3H), 4.12 (q,2H), |
| | | | | | | | | 5.94 (s,1H) |
| 318 | | | | | | | | 0.87 (d,6H), 4.1 (q,2H), 5.88 (s,1H) |
| 320 | | | | | | | | 1.45 (d,3H), 3.27 (s,3H), 6.13 (s,1H) |
| 321 | | | | | | | | 0.97 (t,3H), 1.46 (d,3H), 3.3 (s,3H), |
| | | | | | | | | 6.18 (s,1H), 7.5 (t,2H), 7.68 (t,1H), |
| | | | | | | | | 8.05 (d,2H) |
| 322 | | | | | | | | 0.97 (t,3H), 1.28 (s,9H), 1.48 (d,3H), |
| | | | | | | | | 3.3 (s,3H), 6.13 (s,1H) |
| 323 | | | | | | | | 0.91 (t,3H), 3.32 (s,3H), 6.18 (s,1H) |
| 336 | | | | | | | | 0.9 (t,3H), 1.0 (t,3H), 1.25 (d,6H), |
| | | | | | | | | 4.5 (d,2H), 6.0 (s,1H) |
| 337 | | | | | | | | 0.91 (t,3H), 1.25 (s,9H), 1.27 (d,6H), |
| | | | | | | | | 1.72 (d,3H), 6.0 (s,1H) |
| 338 | | | | | | | | 0.94 (t,3H), 1.27 (d,6H), 1.54 (d,3H), |
| | | | | | | | | 6.04 (s,1H), 7.5 (t,2H), 8.03 (t,2H) |
| 339 | | | | | | | | 0.88 (t,3H), 1.0 (t,3H), 1.28 (d,6H), |
| | | | | | | | | 1.7 ("6",2H), 4.12 (q,2H), 5.98 (s,1H) |
| 340 | | | | | | | | 0.96 (t,3H), 1.27 (d,6H), 3.98 (q,2H), |
| | | | | | | | | 6.03 (s,1H) |
| 341 | | | | | | | | 0.91 (t,3H), 1.25 (s,9H, 1.27 (d,6H), |

TABLE 2-continued

| | Elemental analyses and $^1$H—NMR data of selected active ingredients | | | | | | |
|---|---|---|---|---|---|---|---|
| Active ingredient | Elemental analysis | | | | | | |
| No. | C | H | N | S | Cl | Br | $^1$H—NMR data |
| | | | | | | | 4.1 (q,2H), 5.98 (s,1H) |

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of year, the plants to be combated and their growth stage, and varies from 0.01 to 3.0, and preferably from 0.05 to 1.0, kg/ha.

The novel active ingredients may be applied for instance in the form of directly sprayable solutions, powders, suspensions (including high-percentage aqueous, oily or other suspensions), dispersions, emulsions, oil dispersions, pastes, dusts, broadcasting agents or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, and paraffin, tetrahydrocarbons such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensation products of sulfonated naphthalene and naphthalene derivatives with formaldehyde, condensation products of naphthalene or naphthalenesulfonic acids with phenol or formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate and ureas, and vegetable products such as grain flours, bark meal, wood meal and nutshell meal, cellulosic powders, etc.

Examples of such formulations are given below.

I. 90 parts by weight of the compound of Example 1 is mixed with 10 parts by weight of N-methylpyrrolidone. A solution is obtained suitable for application in the form of very fine drops.

II. 20 parts by weight of compound no. 33 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly dispersing it therein, an aqueous dispersion is obtained.

III. 20 parts by weight of compound no. 34 is dissolved in a mixture consisting of 30 parts by weight of cyclohexanone, 30 parts by weight of isobutanol, and 20 parts by weight of the adduct of 40 moles of ethylene oxide and 1 mole of castor oil. By pouring the solution into water and finely dispersing it therein, an aqueous dispersion is obtained.

IV. 20 parts by weight compound no. 36 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly dispersing it therein, an aqueous dispersion is obtained.

V. 20 parts by weight of compound no. 33 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly dispersing the mixture in water, a spray liquor is obtained.

VI. 5 parts by weight of compound no. 34 is intimately mixed with 95 parts by weight of particulate kaolin. A dust is obtained containing 5% by weight of active ingredient.

VII. 30 parts by weight of compound no. 36 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 33 is intimately mixed with 30 parts of the sodium salt of a phenolsulfonic acid-ureaformaldehyde condensate, 2 parts of silica gel and 48 parts of water. A stable aqueous dispersion is obtained.

IX. 20 parts of the compound obtainable in accordance with Example 1 is intimately mixed with 2 parts of the calcium salt of dodecylbenzenesulfonic acid, 8 parts of a fatty alcohol polyglycol ether, 2 parts of the sodium salt of a phenolsulfonic acid-ureaformaldehyde condensate and 68 parts of a paraffinic mineral oil. A stable oily dispersion is obtained.

The action of the cyclohexenone derivatives of the formula I on plant growth is illustrated in greenhouse experiments.

The vessels employed were plastic flowerpots having a volume of 300 cm$^3$, and which were filled with a sandy loam containing about 3.0% humus. The seeds of the test plants were sown shallow, and separately, according to species.

For the preemergence treatment, the active ingredients were applied to the surface of the soil immediately after the seeds had been sown. The compounds were emulsified or suspended in water as vehicle, and sprayed through finely distributing nozzles. The application rate was 3.0 kg/ha. After the agents had been applied, the vessels were lightly sprinkler-irrigated to induce germination and growth. Transparent plastic covers were then placed in the vessels until the plants had taken root. The cover ensured uniform germination of the plants, insofar as this was not impaired by the active ingredients.

For the postemergence treatment, the test plants were grown to a height of from 3 to 15 cm, depending on growth form, before being treated. For this treatment, either plants which had been sown directly in the pots and grown there were selected, or plants which had been grown from seedlings and transplanted to the vessels a few days before treatment. The application rates for postemergence treatment were 0.5 and 0.25 kg/ha. No covers were placed on the vessels in this treatment method.

The pots were set up in the greenhouse-species from warmer areas at from 20° to 35° C., and species from moderate climates at 10° to 25° C. The experiments were run for 2 to 4 weeks. During this period the plants were tended and their reactions to the various treatments assessed on a 0 to 100 scale, 100 denoting nonemergence or complete destruction of at least the visible plant parts, and 0 denoting no damage or normal growth.

The plants used for the greenhouse experiments were *Alopecurus myosuroides, Avena sativa, Echinochloa crusgalli, Lolium multiflorum, Medicago sativa, Setaria italica, Setaria viridis, Sinapis alba, Triticum aestivum, Zea mays, Avena fatua, Digitaria sanguinalis,* and *Setaria faberii.*

Active ingredients nos. 154, 155, 153, 156 and 35 exhibit, on preemergence application of 3.0 kg/ha, a strong herbicidal action from plants of the Gramineae family; *Sinapis alba*, as an example of a broadleaved plant, remains uninfluenced.

For combating grassy vegetation, compounds nos. 154 and 155 are suitable when applied postemergence at a rate of 0.25 kg/ha. Broadleaved crops such as alfalfa (*Medicago sativa*) are not damaged. The novel compounds have a selective herbicidal action.

Compounds nos. 33 and 36 may be used postemergence for combating unwanted grassy species in wheat. The crop plants suffer no, or at most slight, damage.

Compounds nos. 30, 31, 26, 27, 28, 65, 68, 5, 6, 7 and 8 are suitable for postemergence use for combating a broad spectrum of unwanted grassy species and are well tolerated by alfalfa.

On postemergence application, compounds nos. 71, 72, 9 and 11 have a good action on unwanted grass species and cause little or no damage to the crop plant wheat.

Postemergence application of low rates of compounds nos. 32, 156, 29 and 31 gives a good herbicidal action on grassy species without damaging alfalfa.

Compounds nos. 33 and 34 are suitable, on postemergence application, for combating unwanted grassy species. They are also (in contrast to compounds nos. 76 and 77 from EP 162 224) tolerated in a graminaceous crop such as wheat.

In view of the number of weeds that can be combated, the tolerance of the active ingredients by crop plants, and the desired influence on their growth, and in view of the numerous application methods possible, the compounds according to the invention may be used in a large number of crop plants.

The following crops may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | jerusalem artichoke |
| *Hevea brasiliensis* | rubber plants |
| *Hordeum vulgare* | barley |
| *Humulus lupulus* | hops |
| *Ipomoea batatas* | sweet potatoes |

| Botanical name | Common name |
| --- | --- |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |

To increase the spectrum of action and to achieve synergistic effects, the cyclohexanone derivatives of the formula I may be mixed among themselves or mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, etc.

It may also be useful to apply the cyclohexenone derivatives of the formula I, or herbicidal agents containing them-either on their own or together with other herbicides-in admixture with other crop protection agents, for example agents for combating pests or phytopathogenic fungi or bacteria. It is also possible to prepare mixtures with mineral salt solutions used to remedy nutritional and trace element deficiencies. Non-phytotoxic oils and oil concentrates may also be added.

We claim:

1. A compound selected from the group consisting of

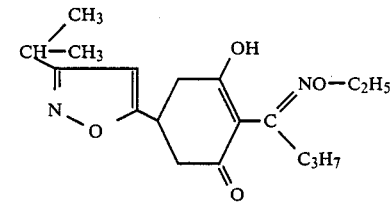

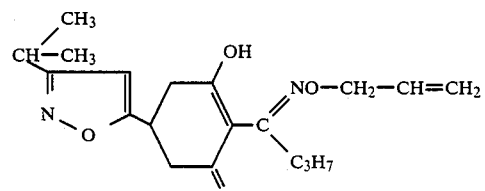

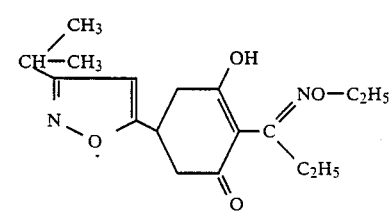

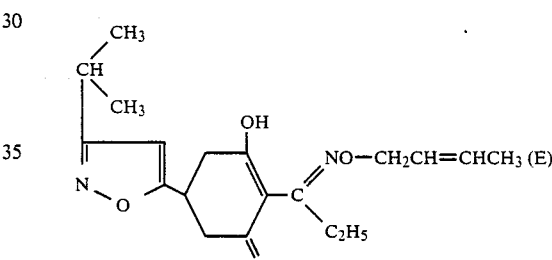

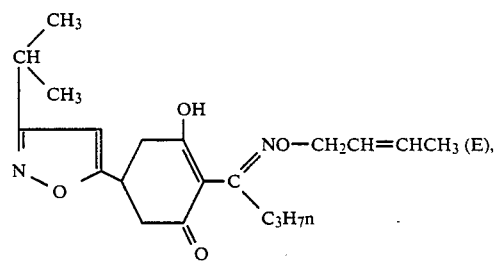

and

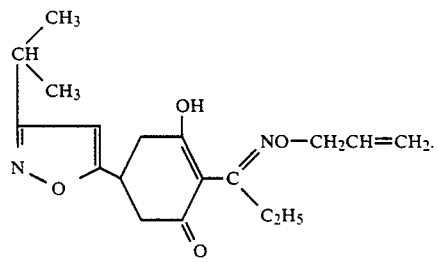

2. A compound according to claim 1, of the formula

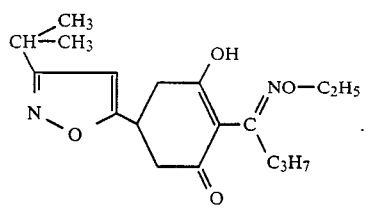

3. A compound according to claim 1, of the formula

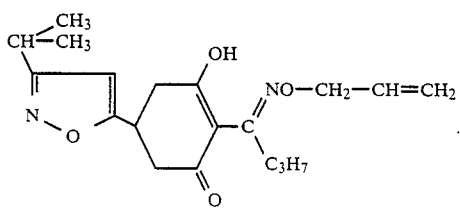

4. A compound according to claim 1, of the formula

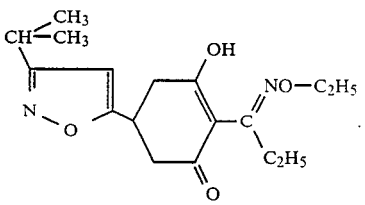

5. A compound according to claim 1, of the formula

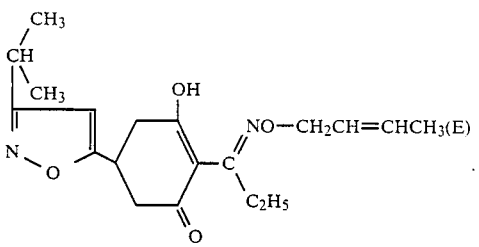

6. A herbicide containing an inert additive and a compound of the formulas according to claim 1.

7. A process for combatting the growth of unwanted plants, wherein the unwanted plants or the area to be kept free from unwanted plant growth are treated with a herbicidally effective amount of a compound of the formulas according to claim 1.

* * * * *